US006465649B1

(12) United States Patent
Gutierrez et al.

(10) Patent No.: US 6,465,649 B1
(45) Date of Patent: Oct. 15, 2002

(54) METHODS FOR THE DEALKYLATION OF PHOSPHONATE ESTERS

(75) Inventors: Arnold J. Gutierrez, San Jose; Ernest J. Prisbe, Los Altos; John C. Rohloff, Mountain View, all of CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 09/641,547

(22) Filed: Aug. 17, 2000

Related U.S. Application Data
(60) Provisional application No. 60/149,571, filed on Aug. 18, 1999.

(51) Int. Cl.$^7$ ............................... C07F 9/02; C07F 9/28
(52) U.S. Cl. ....................... 544/244; 556/404; 556/405; 562/8
(58) Field of Search ................................ 556/404, 405; 562/8

(56) References Cited

PUBLICATIONS

Dhawan et al., "o–Hydroxyaryl Diphosphonic Acids", 49:4018–4021, J Org Chem, 1984.
Ebetino et al., "Mechanisms of Action of Etidronate and Other Bisphosphonates", 9:233–243, Rev. Contemp. Pharmacother., 1998.
Fleisch, H., "Bisphosphonates: Mechanisms of Action and Clinical Use", Chapter 74, pp. 1037–1052, Principles of Bone Biology, 1996.
Goto et al., "Synthesis and Biological Activity of the Metabolites of Diethyl 4–[(4–Bromo–2–cyanophenyl)carbamoyl]benzylphosphonate (NO–1886)", 44(3):547–551, CHEM PHARM BULL, 1996.
Hampton et al., "Synthesis of 6'–Cyano–6'–deoxyhomoadenosine–6'–phosphonic Acid and Its Phosphoryl and Pyrophosphoryl Anhydrides and Studies of Their Interactions with Adenine Nucleotide Utilizing Enzymes", 95(13):4404–4414, J Am Chem Soc, Jun. 27, 1973.
Hanson et al., "Ring Closing Metathesis Reactions on a Phosphonate Template", 39:3939–3942, Tet Lett, 1998.
Holy et al., "Synthesis of 9–(2–Phosphonylmethoxyethyl)Adenine and Related Compounds", 52:2801–2809, Collect Czech Chem Commun, 1987.
Kim et al, "Acyclic Purine Phosphonate Analogues as Antivral Agents. Synthesis and Structure—Activity Relationships", 33:1207–1213, J Med Chem, 1990.

Kluge et al., "Phosphonate Reagents for the Synthesis of Enol Ethers and One–Carbon Homologation to Aldehydes", 44(26):4847–4852, J Org Chem, 1979.
Kosolopoff et al., Chapter 7, p. 139, Organophosphorus Compounds, John Wiley & Sons, New York, NY, 1950.
Machida et al., "A Useful Method for the Dealkylation of Dialkyl Phosphonates", 9(2):97–102, Synthetic Comm, 1979.
Magnin, et al., "1,1–Bisphosphonate Squalene Synthase Inhibitors: Interplay Between the Isoprenoid Subunit and the Diphosphate Surrogate", 38:2596–2605, J Med Chem, 1995.
McKenna et al., "The Facile Dealkylation of Phosphonic Acid Dialkyl Esters by Bromotrimethylsilane", 2:155–158, Tet Lett, 1977.
McKenna et al., "Functional Selectivity in Phosphonate Ester Dealkylation with Bromotrimethylsilane", p. 739, J.C.S. Chem. Comm., 1979.
Morita et al., "A Convenient Dealkylation of Dialkyl Phosphonates by Chlorotrimethylsilane in the Presence of Sodium Iodide", 28:2523–2526, Tet Lett, 1978.
Nakamura et al., "Total Synthesis of (±)–Phosphonothrixin, a Novel Herbicidal Antibiotic Containing C–P Bond", 48(10):1134–1137, The Journal of Antibiotics, Oct. 1995.
Papapoulos et al., "The Use of Bisphosphonates in the Treatment of Osteoporosis", 13:S41–S49, Bone, 1992.
Rabinowitz, "The Reactions of Phosphonic Acid Esters with Acid Chlorides. A Very Mild Reaction", 28:2975–2978, J Org Chem, 1963.
Rowosky et al., "Dual Inhibition of Dihydrofolate Reductase and Folylpolyglutamate Synthetase by Methotrexate and Aminopterin Analogues with a Gamma–Phosphonate Group in the Side Chain", 35(19):3327–3333, Biochem Pharm, 1986.
Schultze et al., "Practical Synthesis of the anti–HIV Drug, PMPA", 39:1853–1856, Tet Lett, 1998.
Tsai et al., "Prevention of SIV Infection in Macaques by (R)–9–(2–Phosphonylmethoxypropyl)adenine", 270:1197–1199, Science, Nov. 17, 1995.

Primary Examiner—Johann Richter
Assistant Examiner—Ebenezer Sackey
(74) Attorney, Agent, or Firm—Max D. Hensley

(57) ABSTRACT

Disclosed are methods for the dealkylation of phosphonate esters by use of trimethylchlorosilane as the dealkylating agent. In particular, this invention is directed to the discovery that high yields for the dealkylation of phosphonate esters can be achieved within relatively short reaction times by the use of trimethylchlorosilane provided that the dealkylation procedure occurs in a sealed vessel containing a compatible solvent.

13 Claims, No Drawings

METHODS FOR THE DEALKYLATION OF PHOSPHONATE ESTERS

This application claims benefit to provisional application No. 60/149/571 filed Aug. 18, 1999.

BACKGROUND OF THE INVENTION

Field of the Invention

This invention is directed to methods for the dealkylation of phosphonate esters by use of trimethylchlorosilane as the dealkylating agent. In particular, this invention is directed to the discovery that high yields for the dealkylation of phosphonate esters can be achieved within relatively short reaction times by the use of trimethylchlorosilane provided that the dealkylation procedure occurs in a compatible solvent. In a preferred embodiment, the reaction is conducted in a sealed container.

This invention is further directed to novel compositions used in the methods of this invention.

References

The following publications are cited in this application as superscript numbers:

[1] Kim, et al., *Acyclic Purine Phosphonate Analogues as Antiviral Agents. Synthesis and Structure-Activity Relationships*, J. Med. Chem., 33:1207–1213 (1990)
[2] Schultze, et al., *Practical Synthesis of the anti-HIV Drug, PMPA*, Trahedron Letters, 39:1853–1856 (1998)
[3] Tsai, et al., *Prevention of SIV Infection in Macaques by (R)-9-(2-Phosphonylmethoxypropyl)adenine*, Science, 270:1197–1199
[4] Kosolopoff, et al., *Organophosphorus Compounds*, John Wiley & Sons, New York, N.Y. (1950)
[5] McKenna, et al., *Functional Selectivity in Phosphonate Ester Dealkylation with Bromotrimethylsilane*, J.C.S. Chem. Comm., p. 739 (1979)
[6] McKenna, et al., *The Facile Dealkylation of Phosphonic Acid Dialkyl Esters by Bromotrimethylsilane*, Tetrahedron Letters, 2:155–158 (1977)
[7] Rabinowitz, *The Reactions of Phosphonic Acid Esters with Acid Chlorides. A Very Mild Reaction*, J. Org. Chem., 28:2975–2978 (1963)
[8] Machida, et al., *A Useful Method for the Dealkylation of Dialkyl Phosphonates*, Synthetic Communications, 9(2):97–102 (1979)
[9] Morita, et al., *A Convenient Dealkylation of Dialkyl Phosphonates by Chlorotrimethylsilane in the Presence of Sodium Iodide.*, Tetrahedron Letters, 28:2523–2526 (1978)
[10] Klug, et al., J. Org. Chem., 44:4847 (1979)
[11] Hampton, et al., J. Am. Chem. Soc., 95:4404–4414
[12] Holy, et al., Collect. Czech. Chem. Commun., 52:2801–2809 (1987)
[13] Papapoulos, et al., Bone, 13:S41–S49 (1992)
[14] Ebetino, et al., Rev. Contemp. Pharmacother., 9:233–243 (1998)
[15] Bilezikian, et al., Bone Biol., 1037 (1996)
[16] Nakumura, et al., Journal of Antibiotics, 48:1134 (1995)
[17] Magnin, et al., J. Med. Chem., 38:2596 (1995)
[18] Goto, et al., Chem. Pharm. Bull., 44:547 (1996)
[19] Rowosky, et al., Biochem. Pharmacol., 35:3327 (1986)

All of the above publications are herein incorporated by reference in their entirety to the same extent as if each individual publication was specifically and individually indicated to be incorporated by reference in its entirety.

STATE OF THE ART

Numerous antiviral agents described in the literature are phosphonate compounds. Examples of such antiviral compounds include acyclic purine phosphonates as described by Kim et al.[1] and 9-[2-(phosphonomethoxy)ethyl]-adenine and R-9-[2-(phosphonomethoxy)propyl]adenine as described by Schultze, et al.[2,3].

Phosphonate compounds have also been described for use in treating bone degeneration/osteoporosis[13-15], in relationship to platlet activating factors, herbicical antibiotics[16], in relationship to cholesterol drugs[17-18], and with antineoplastic agents.[19] Accordingly, phosphonate compounds have a wide diversity of uses in the medicinal arts.

Such phosphonates can be represented by the general formula:

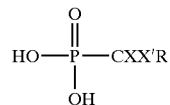

where X and X' are independently selected from hydrogen, alkyl and halogen and R is selected from the group consisting of alkyl, substituted alkyl, alkoxy, substituted alkoxy, cycloalkyl, substituted cycloalkyl, aryl, heteroaryl and heterocyclic. Preferred antiviral phosphonate compounds are represented by the formula:

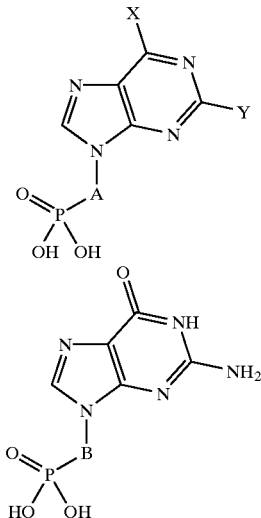

wherein A and B are, for example, alkylene, substituted alkylene, alkylene-O-alkylene, or alkylene-S-alkylene; X is, for example, hydrogen, hydoxyl or amino; and Y is, for example, hydrogen or amino.

The synthesis of these phosphonates typically proceeds through intermediates employing phoshonate esters which are employed as blocking or protecting groups. Subsequent removal of these groups reestablishes the phosphonate functionality which typically occurs as the terminal step in the synthesis. Conventional methods for dealkylating phosphonate esters include reaction with aqueous solutions of concentrated HCl or HBr. However, many of the functional groups on the phosphonates are acid labile which cannot tolerate these harsh acidic conditions.[4]

Milder reagents to effect dealkylation are trialkylsilylhalides which selectively cleave PO alkylesters yielding trialkylsilyl esters which are readily hydrolyzed with water (pH~7). Trimethylbromosilane (TMSBr) is the most commonly used reagent in this class due to its high reactivity and chemoselectivity.[5,6] However, the use of trimethylbromosilane requires special handling procedures due its high corrosivity (relative to trimethyl-chlorosilane) and this compound is approximately three times more expensive than the corresponding trimethylchlorosilane. Such differences provide a compelling basis to employ trimethylchlorosilane as the reagent of choice in the dealkylation of phosphonate esters.

Notwithstanding the above, the use of trimethylchlorosilane as a dealkylation reagent in reactions with phosphonate esters has been hindered by its poor reactivity (relative to trimethylbromosilane). In this regard, the literature is replete with references stating that prolonged reaction times and/or poor yields arise from use of trimethylchlorosilane in such dealkylation reactions.[6-9]

In order to address this problem, it has been reported that the addition of either sodium or lithium iodide to the reaction medium results in substantially faster reaction times and provided high yields of the product.[8,9] However, the addition of such salts was also reported to lead to contamination of the resulting phosphonate product with lithium halide salts requiring crystallization of this product as its monoanilinium salt to effect removal of this salt.[8]

In view of the above, methods to efficiently effect dealkylation of phosphonate esters in high yield with trimethylchlorosilane would be particularly desirable. Preferably, such methods would not employ alkali iodide salts such that purification of the resulting products would be simplified.

SUMMARY OF THE INVENTION

This invention is based on the novel and unexpected discovery that dealkylation of phosphonate esters using trimethylchlorosilane can be consistently achieved for a wide variety of ester groups in the absence of added alkali iodide salts by use of a solvent. In experiments reported below, the combination of trimethylchlorosilane and solvent provided for almost quantitative recovery of dealkylated product in approximately 10% of the time required by prior art processes employing no solvent. Subsequent hydrolysis of the trialkylsilyl phosphonate provided for desired phosphonate in almost quantitative amounts.

In view of the above, this invention is directed to methods for dealkylation of phosphonate esters using trimethylchlorosilane as the dealkylating agent. Specifically, in a first method aspect, this invention is directed to a method for dealkylation of phosphonate esters which method comprises:

(a) combining a phosphonate ester and trimethylchlorosilane in a solvent in the absence of alkali iodide salts; and (b) maintaining the resulting reaction mixture under conditions wherein the phosphonate ester is converted to trimethylsilyl phosphonate.

In one preferred embodiment, the reaction is conducted in a sealed reaction vessel.

In another preferred embodiment, the trimethylsilyl phosphonate is subsequently hydrolyzed in an aqueous solution under conditions which provide for the phosphonic acid [i.e., $R^1$ and $R^2$ (if present) are hydrogen].

In still another preferred embodiment, the methods of this invention are employed to dealkylate bisphosphonate esters (i.e., compounds of formula I wherein both $R^1$ and $R^2$ are other than hydrogen).

In another of its method aspects, this invention is directed to a method for dealkylation of phosphonate esters which method comprises:

(a) adding a phosphonate ester to a solvent within a sealable container;

(b) adding trimethylchlorosilane to the sealable container defined in (a) above;

(c) sealing the container;

(d) maintaining the sealed container under conditions wherein the phosphonate ester is converted to silyl phosphonate; and (e) hydrolyzing the silyl phosphonate to provide for the dealkylated phosphonic acid or a salt thereof.

Preferably, the phosphonate ester is represented by a compound of either formula I or II:

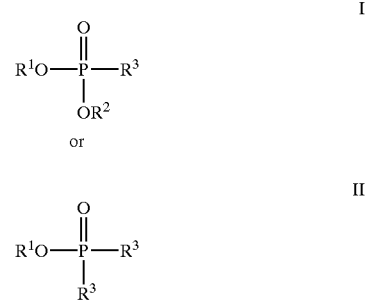

wherein $R^1$ and $R^2$ are independently selected from the group consisting of hydrogen, alkyl, substituted alkyl, alkenyl, substituted alkenyl, alkynyl, substituted alkynyl, cycloalkyl, substituted cycloalkyl, aryl, heteroaryl and heterocyclic; and $R^3$ is an organic moiety linked to the phosphorous atom by a carbon atom. Typically, $R^3$ is selected from the group consisting of alkyl, substituted alkyl, alkenyl, substituted alkenyl, alkynyl, substituted alkynyl, alkylene-O-alkyl, substituted alkylene-O-alkyl, alkylene-O-substituted alkyl, substituted alkylene-O-substituted alkyl, alkylene-S-alkyl, substituted alkylene-S-alkyl, alkylene-S-substituted alkyl, substituted alkylene-S-substituted alkyl, alkylene-O-alkyenyl, alkylene-O-substituted alkyenyl, aryl, heteroaryl and heterocyclic and salts thereof and with the proviso that, in formula I, at least one of $R^1$ and $R^2$ is other than hydrogen and in formula II, $R^1$ is not hydrogen.

Preferred $R^3$ groups include, by way of example only, alkylene-O-alkylene-B, alkylene-O-substituted alkylene-B, alkylene-O-alkenylene-B and alkylene-O-substituted alkenylene-B which are exemplified by the groups which include —$CH_2OCH(CH_3)CH_2B$, —$CH_2OCH(CH_2OH)CH_2B$, —$CH_2OCH(CH_2N_3)CH_2B$, —$CH_2OCH(CH_2F)CH_2B$, —$CH_2OCH(C\equiv CH)CH_2B$ and —$CH_2OCH(CH=CH_2)CH_2B$ where B is a base such as adenine, guanine, guanosine, cytosine, thymine, inosine, uridine, thiouridine, and substituted variants thereof wherein such bases are substituted with 1–4 substituents selected from substituents recited for substituted heteroaryl groups.

Particularly preferred phosphonate esters for use in this invention are represented by the formula:

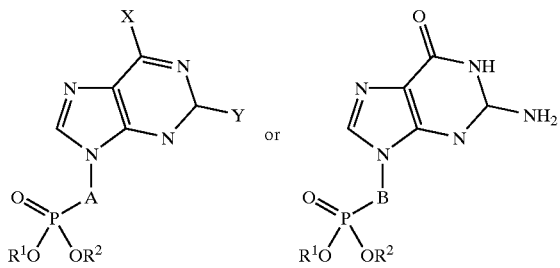

wherein $R^1$ and $R^2$ are as defined above, A and B are selected from the group consisting of alkylene, substituted alkylene, alkylene-O-alkylene, alkylene-O-substituted alkylene, substituted alkylene-O-alkylene, substituted alkylene-O-substituted alkylene, alkylene-S-alkylene, substituted alkylene-S-alkylene, alkylene-S-substituted alkylene, substituted alkylene-S-substituted alkylene, alkylene-O-alkenylene, alkylene-O-substituted alkenylene, substituted alkylene-O-alkenylene, substituted alkylene-O-substituted alkenylene, alkylene-S-alkenylene, substituted alkylene-S-alkenylene, alkylene-S-substituted alkenylene, and substituted alkylene-S-substituted alkenylene; X is selected from the group consisting of hydrogen, hydoxyl and amino; and Y is selected from the group consisting of hydrogen and amino.; X is selected from the group consisting of hydrogen, hydoxyl and amino; and Y is selected from the group consisting of hydrogen and amino.

Even more preferred phosphonate esters are represented by formulas III and IV below:

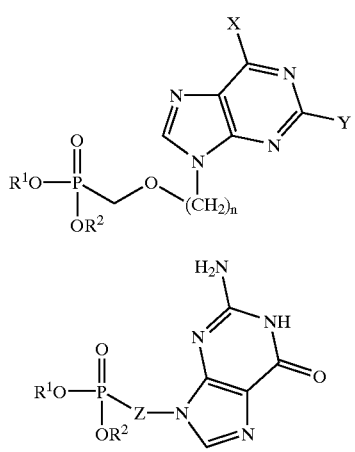

III

IV wherein $R^1$, $R^2$, X and Y are as defined above; Z is selected from the group consisting of alkylene, substituted alkylene and alkylene-O-alkylene; and n is an integer of from 1 to 10.

Specific phosphonate esters include those defined in Tables I and II below:

TABLE I

| PHOSPHONATES OF FORMULA III | | |
|---|---|---|
| X | Y | n |
| OH | $NH_2$ | 2 |
| $NH_2$ | H | 2 |

TABLE I-continued

| PHOSPHONATES OF FORMULA III | | |
|---|---|---|
| X | Y | n |
| OH | $NH_2$ | 3 |
| $NH_2$ | H | 3–7 |
| $NH_2$ | $NH_2$ | 4–7 |
| OH | $NH_2$ | 4–7 |

TABLE II

| PHOSPHONATES OF FORMULA IV |
|---|
| Z |
| $-(CH_2)_4-$ |
| $-(CH_2)_2-O-CH_2-$ |
| $-CH_2-S-(CH_2)_2-$ |
| $-CF_2(CH_2)_3-$ |
| $-CH_2-O-CH_2-$ |
| $CH(CH_3)-$ |

In still another of its method aspects, this invention is directed to a method for dealkylation of bisphosphonate esters which method comprises:

(a) adding a bisphosphonate ester to a solvent within a sealable container wherein the bisphosphonate ester is represented by formulas below:

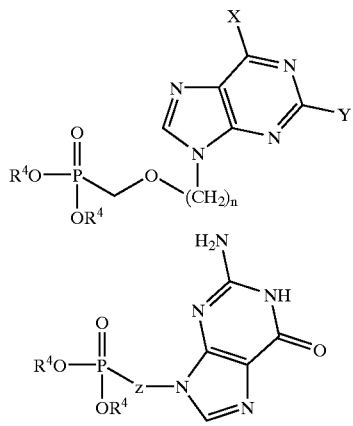

wherein each $R^4$ is independently selected from the group consisting of alkyl, substituted alkyl, alkenyl, substituted alkenyl, alkynyl, substituted alkynyl, cycloalkyl, substituted cycloalkyl, aryl, heteroaryl and heterocyclic, and X, Y, Z and n are as defined above;

(b) adding trimethylchlorosilane to the sealable container defined in (a) above;

(c) sealing the container;

(d) maintaining the sealed container under conditions wherein the bisphosphonate ester is converted to bis(silyl) phosphonate of the formula:

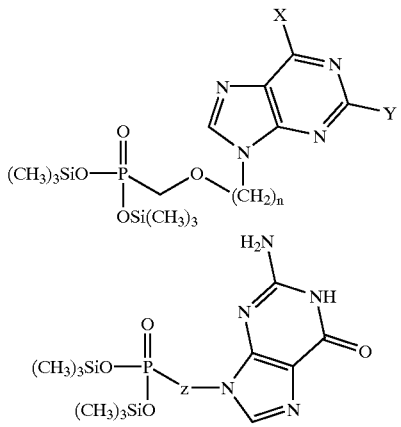

wherein X, Y, Z and n are as defined above; and
(e) hydrolyzing the bis(silyl) phosphonate to provide for the phosphonates of the formula:

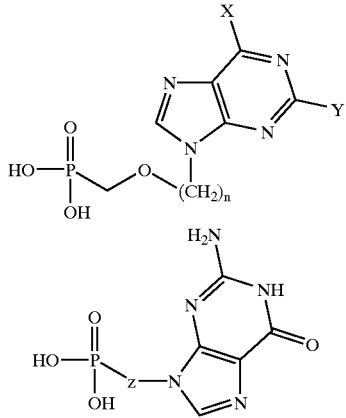

wherein X, Y, Z and n are as defined above; and salts thereof.

Preferably, the salts of such compounds are pharmaceutically acceptable salts.

In one preferred embodiment, the solvent is selected from the group consisting of chlorobenzene, dimethylformamide, acetonitrile, dichloroethane, n-butylchloride, 2-butylchloride, n-pentylchloride, 2-chloropentane, 1-chlorooctane, trichloroethane, chloroform, cyclopentylchloride, chlorocyclohexane, chlorobenzene, 2-chlorotoluene, o-dichlorobenzene, 1-chloronaphthlene, 4-chlorobenzotrichloride, 2-chlorobenzotrifluoride, 3-chlorobenzotrifluoride, 4-chlorobenzotrifluoride, chlorodibromomethane, chlorodibromofluoromethane, benzene, toluene, o-xylene, propionitrile, valeronitrile, benzonitrile, dimethylacetamide, dimethylpropionamide, 1-methylpyrrolidin-2-one, methyl acetate, ethyl acetate, isopropyl acetate, methyl propionate, ethyl propionate, methyl butyrate, ethyl butyrate, methyl caproate, ethyl caproate, butyl acetate, ethyl isovalerate, methyl ethyl ketone, ethyl propyl ketone, methyl iso-butyl ketone, 3-methyl-2-butanone, methyl iso-amyl ketone, and the like.

In one preferred embodiment, the solvent is selected to have a dielectric constant of greater than about 5. In another preferred embodiment, the solvent is selected to have a polarity index of greater than about 2.5. Even more preferably, the solvent is selected to have a boiling point of greater than about 60° C.

In another preferred embodiment, the reaction is conducted in the absence of added iodide salts such as lithium iodide and sodium iodide. "Absence" of iodide salts means that insufficient iodide salt is present to detectably change the rate of dealkylation by greater that 10%, preferably 0%, at any point in the reaction.

In one of its composition aspects, this invention is directed to a composition comprising a phosphonate ester, trimethylchlorosilane and a solvent with the proviso that said composition does not include any alkali iodide salts.

DETAILED DESCRIPTION OF THE INVENTION

As noted above, this invention is directed to methods for the dealkylation of phosphonate esters by use of trimethylchlorosilane as the dealkylating agent. However, prior to defining this invention in further detail, the following terms will first be defined. Any terms not defined herein have their art recognized meanings.

Definitions The term "solvent" refers to aprotic solvents, i.e. aprotic polar or nonpolar solvents. "Solvent" includes those solvents which solubilize at least one phosphonate ester, preferably at least at a level of 30 mg/mL. The solvent is preferably selected from the group consisting of chlorobenzene, dimethyl-formamide, acetonitrile, dichloroethane, n-butylchloride, 2-butylchloride, n-pentylchloride, 2-chloropentane, 1-chlorooctane, trichloroethane, chloroform, cyclopentyl-chloride, chlorocyclohexane, chlorobenzene, 2-chlorotoluene, o-dichlorobenzene, 1-chloronaphthlene, 4-chlorobenzotrichloride, 2-chlorobenzotrifluoride, 3-chlorobenzotrifluoride, 4-chlorobenzotrifluoride, chlorodibromomethane, chlorodibromofluoromethane, benzene, toluene, o-xylene, propionitrile, valeronitrile, benzonitrile, dimethylacetamide, dimethylpropionamide, 1-methylpyrrolidin2-one, methyl acetate, ethyl acetate, isopropyl acetate, methyl propionate, ethyl propionate, methyl butyrate, ethyl butyrate, methyl caproate, ethyl caproate, butyl acetate, ethyl isovalerate, methyl ethyl ketone, ethyl propyl ketone, methyl iso-butyl ketone, 3-methyl-2-butanone, methyl iso-amyl ketone, and the like. Suitable solvents can be readily determined merely by assessing their utility in the methods of this invention as exemplified in the examples below. Particularly preferred solvents include, for example, chlorobenzene, dimethylformamide, acetonitrile and dichloroethane.

Preferably, the solvent is selected to have a dielectric constant of greater than about 5 or a polarity index of greater than about 2.5.

More preferably, the solvent is selected to have a boiling point of greater than about 60° C.

The term "sealable container" refers to containers which exhibit a leakage of less than 5 psi per hour with an initial pressure of 50 psi. Preferably, the sealable container exhibits a leakage of less than 2 psi per hour with an initial pressure of 50 psi. More preferably, the sealable container exhibits a leakage of less than 1 psi per hour with an initial pressure of 50 psi.

The term "alkyl" refers to a monoradical branched or unbranched saturated hydrocarbon chain preferably having from 1 to 10 carbon atoms and more preferably 1 to 6 carbon atoms. This term is exemplified by groups such as methyl, ethyl, n-propyl, iso-propyl, n-butyl, iso-butyl, n-hexyl and n-decyl and the like.

The term "substituted alkyl" refers to an alkyl group as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. This term is exemplified by groups such as hydroxymethyl, hydroxyethyl, hydroxypropyl, 2-aminoethyl, 3-aminopropyl, 2-methylaminoethyl, 3-dimethylaminopropyl, 2-sulfonamidoethyl, 2-carboxyethyl, and the like.

The term "alkylene" refers to a diradical of a branched or unbranched saturated hydrocarbon chain, preferably having from 1 to 10 carbon atoms and more preferably 1 to 6 carbon atoms. This term is exemplified by groups such as methylene (—CH$_2$13 ), ethylene (—CH$_2$CH$_2$—), the propylene isomers (i.e., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkenyl" refers to a monoradical of a branched or unbranched unsaturated hydrocarbon group preferably having from 2 to 10 carbon atoms and more preferably 2 to 6 carbon atoms and having at least 1 and preferably from 1–6 sites of vinyl unsaturation. Preferred alkenyl groups include ethenyl (—CH═CH$_2$), n-propenyl (—CH$_2$CH═CH$_2$), iso-propenyl (—C(CH$_3$)═CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 10 carbon atoms and more preferably 2 to 6 carbon atoms and having at least 1 and preferably from 1–3 sites of vinyl unsaturation. This term is exemplified by groups such as ethenylene (—CH═CH—), the propenylene isomers (e.g., —CH$_2$CH═CH— and —C(CH$_3$)═CH—) and the like and includes all positional isomers such as cis and trans isomers.

The term "substituted alkenylene" refers to an alkenylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkynyl" refers to a monoradical of an unsaturated hydrocarbon preferably having from 2 to 10 carbon atoms and more preferably 2 to 6 carbon atoms and having at least 1 and preferably from 1–2 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

The term "acyl" refers to the groups HC(O)—, alkyl-C(O)—, substituted alkyl-C(O)—, alkenyl-C(O)—, substituted alkenyl-C(O)—, cycloalkyl-C(O)—, substituted cycloalkyl-C(O)—, cycloalkenyl-C(O)—, substituted cycloalkenylC(O)—, aryl-C(O)—, heteroaryl-C(O)— and heterocyclic—C(O)— where alkyl, substituted alkyl, alkenyl, substituted alkenyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "sulfonylamino" refers to the group —NRSO$_2$R$^a$ where R is hydrogen, alkyl, substituted alkyl, aralkyl, or heteroaralkyl, and R$^a$ is alkyl, substituted alkyl, amino, or substituted amino wherein alkyl, substituted alkyl, aralkyl, heteroaralkyl and substituted amino are as defined herein.

The term "aminoacyl" refers to the group —NRC(O)R where each R is independently hydrogen, alkyl, substituted alkyl, alkenyl, substituted alkenyl, amino, substituted amino, aryl, heteroaryl, or heterocyclic wherein alkyl, substituted alkyl, alkenyl, substituted alkenyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). The aryl group may optionally be fused to a heterocyclic or cycloalkyl group. Preferred aryls include phenyl, naphthyl and the like. Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, sulfonylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "amino" refers to the group —NH$_2$.

The term "substituted amino" refers to the group —NRR where each R is independently selected from the group consisting of hydrogen, alkyl, substituted alkyl, acyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cycloalkyl" refers to cyclic alkyl groups of from 3 to 20 carbon atoms having a single cyclic ring or multiple condensed rings, said cycloalkyl group may optionally be fused to an aryl or heteroaryl group. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkyl, substituted alkyl, alkenyl, substituted alkenyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkyl, substituted alkyl, alkenyl, substituted alkenyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring). The heteroaryl ring may optionally be fused to a cycloalkyl or heterocyclyl ring. Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred heteroaryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "heteroaryloxy" refers to the group heteroaryl-O—.

The term "heterocycle" or "heterocyclyl" refers to a monoradical saturated unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring and further wherein one, two, or three of the ring carbon atoms may optionally be replaced with a carbonyl group (i.e., a keto group). Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO—alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Examples of heteroaryls and heterocycles include, but are not limited to, pyrrole, thiophene, furan, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, pyrrolidine, piperidine, piperazine, indoline, morpholine, tetrahydrofuranyl, tetrahydrothiophene, and the like as well as N-alkoxy-nitrogen containing heterocycles.

The term "heterocyclooxy" refers to the group heterocyclic-O—.

The term "thioheterocyclooxy" refers to the group heterocyclic-S—.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" or "alkylthio" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

Methodology

The methods of this invention may be conducted by the following methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

Specifically, dealkylation and hydrolysis of phosphonate esters involve a two-step procedure as shown in reaction (1) below. Reaction (1) depicts for illustrative purposes only dealkylation and hydrolysis of bisphosphonate esters and, it is understood, of course, that other phosphonates can be similarly dealkylated (e.g., $R^1$ being an ester and $R^2$ being hydrogen). In any event, reaction (1) is illustrated as follows:

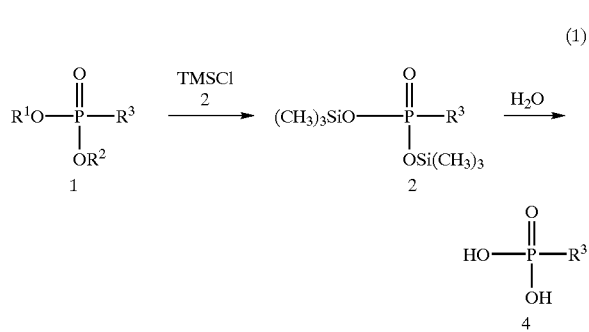

wherein $R^1$, $R^2$ and $R^3$ are as defined above and TMSCl refers to trimethyl-chlorosilane.

In reaction (1), phosphonate ester 1 is combined with a solvent preferably in a sealable container such as, for example, a glass pressure reactor preferably containing a thermowell and a pressure gauge. The reaction can also be conducted on an industrial scale using a Pfaulder reactor as a sealable container. The particular sealable container employed is not critical and the selection of a suitable sealable containers is well within the skill of the art.

The amount of solvent employed in this reaction preferably ranges from about 50 to about 90 weight percent of the total weight of the solvent plus phosphonate ester 1 and more preferably from about 60 to about 80 weight percent.

Preferably, at least a stoichiometric equivalent of trimethylchlorosilane 2 per each ester present on phosphonate ester 1 is added to the sealable container in order to effect dealkylation of the ester functionalities on the phosphonate ester. In one preferred embodiment, trimethylchlorosilane 2 is employed at from about 1.5 to about 2 equivalents relative to each ester present on phosphonate ester 1. It is understood, of course, that an excess of trimethylchlorosilane 2 will speed reaction completion and, accordingly, an excess of this reagent is often employed in sluggish reactions.

After all of the reagents have been added, the container is preferably sealed and then maintained under conditions to effect dealkylation of the phosphonate ester to provide for the (silyl) phosphonate 3. Preferably, the reaction proceeds under an inert atmosphere (e.g., nitrogen or argon) by heating the container to a temperature of from about 90° C. to about 140° C. Heating is continued until the reaction is complete which typically occurs within about 2 to 60 hours.

After reaction completion, hydrolysis of silyl phosphonate 3 to phosphonic acid 4 is readily achieved by the addition of water to the reaction mixture. In one embodiment, the solvent is first removed from the silyl phosphonate 3 by evaporation and then water is added to the residue to effect hydrolysis. Preferably, however, water is added directly to the reaction mixture and vigorous stirring is employed to effect hydrolysis in situ. The reaction proceeds rapidly and the resulting phosphonic acid 4 is recovered by conventional means such as chromatography, filtration, distillation, etc.

If desirable, phosphonic acid 4 can be converted to a salt thereof such as a pharmaceutically acceptable salt by conventional methods well known in the art.

The methods of this invention employ novel compositions. Accordingly, this invention is also directed to such novel compositions which comprise a phosphonate ester, trimethylchlorosilane and a solvent with the proviso that said composition does not include any alkali iodide salts.

Utility

The methods of this invention are useful in dealkylation of phosphonate esters. Such esters are well known intermediates in the synthesis of a variety of medicaments including anti-viral agents, anti-neoplastic agents, and herbicical antibiotics, medicaments used in treating bone degeneration/osteoporosis, and medicaments used in relationship to platlet activating factors and cholesterol drugs. Accordingly, the methods of this invention are useful in the synthesis of such medicinal agents.

EXAMPLES

The following examples illustrate the methods of this invention. In these examples, all temperatures are in degrees Celcius (unless otherwise stated) and the following abbreviations have the following meanings:

DMF=dimethylformamide
eq.=equivalents
g=grams
h=hours
kg=kilogram
L=liters
M=molar
mL=milliliters
NMR=nuclear magnetic resonance
PMEA=9-[2-(phosphonomethoxy)ethyl]adenine
PMPA=(R)-9-[2-(phosphonomethoxy)propyl]adenine
psi=pounds per square inch
RT=room temperature
TMSBr=trimethylbromosilane
TMSCl=trimethylchlorosilane Example 1

This example assesses the ability of TMSCl to cleave a variety of phosphonate esters using a solvent and a sealed reaction vessel according to reaction (1) below:

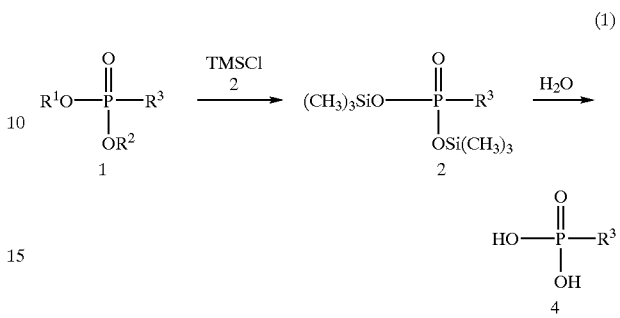

(1)

Specifically, 1.0 M solutions of 1 in chlorobenzene were mixed with TMSCl in sealed glass pressure tubes and heated at temperatures ranging from 130–140° C. As substitution to 2 progressed, modest increases in the internal pressure of the reaction vessels were observed due to the formation of volatile alkylchloride. The pressure reached a maximum at reaction completion, then returned to atmospheric pressure on cooling back to room temperature.

The conversions of 2 to phosphonic acids 4 were monitored by evaporating an aliquot of the reaction mixture, adding $D_2O$ and observing the resulting formation of phosphonic acids 4 by $^1H$ and $^{31}P$ NMR[4] (Table III).

TABLE III

Clevage of dialkylphosphonates 1 with chlorotrimethylsilane

| Phosphonate | R¹ | R²/R³ | TMSCl (eq.) | ° C. | hr | % Conv. |
|---|---|---|---|---|---|---|
| 1a | $CH_3OOCCH_2$ | $CH_3$ | 3 | 130 | 8 | 98 |
| 1b | $C_2H_5OOCCH_2$ | $C_2H_5$ | 4 | 140 | 18 | 98 |
| 1c | $C_2H_5OOCCH_2$ | $(CH_3)_2CH$ | 6 | 140 | 36 | 98 |
| 1d | $C_6H_5OCCH_2$ | $C_2H_5$ | 4 | 140 | 12 | 98 |
| 1e | $C_6H_5CH_2$ | $C_2H_5$ | 4 | 140 | 10 | 99 |
| 1f | $CH_2=CH$ | $C_2H_5$ | 4 | 140 | 10 | 98 |
| 1g | $CH_3OCH_2CH_2OCH_2$ | $C_2H_5$ | 4 | 140 | 8 | >99 |

As per Table III, phosphonate esters containing several functional groups were evaluated for ease of dealkylation and compatibility to the reaction conditions. Specifically, phosphonate esters 1a–1g recited in Table III above were prepared according to the procedures recited by Kluge, et al.[10] Each of these phosphonate esters 1a–1g were combined with TMSCl in chlorobenzene at 130–140°, followed by hydrolysis to provide for complete conversions to phosphonic acids (Table III).

In most cases, dealkylation was complete in 8 to 12 h, however times increased at lower reaction temperatures. The high percent conversions to phosphonic acid 4 show that a variety of functional groups including carboxylic esters, ethers and alkenes are compatible with these conditions. Among the compounds evaluated, the more labile dimethylphosphonate 1a was the most easily deprotected by TMSCl in chlorobenzene. However, diethylphosphonates 1b. 1d–g were also completely cleaved after slightly longer heating times and even the more hindered isopropyl ester groups of 1c were removed if a greater excess of TMSCl was used. These rates of cleavage are consistent with their rates of cleavage by TMSBr.

The heating time required for dealkylation of diethylphosphonates 1e and 1f with TMSCl in chlorobenzene was 10 h. By comparison, dealkylation of 1e and 1f with TMSCl, in the absence of solvent, are reported in the literature to afford the corresponding phosphonic acids 3e and 3f after 4 and 5 days respectively.[7] The deprotections with TMSCl also proceeded well in DMF, acetonitrile, and dichloroethane, however the latter two solvents produce higher reaction vessel pressures.

Example 2

This example illustrates dealkylation of two specific phosphonate esters. Specifically, PMEA 7 and PMPA 8 are broad spectrum antivirals including potent and selective activity against human immunodefficiency virus.[2,3] One reported synthesis of 7 and 8 utilizes TMSBr for cleavage to the phosphonic acids from the diethylesters 5 and 6.[2]

By comparison, the same deprotections were performed with TMSCl (reaction 2) affording 7 and 8 in equivalent yields and purities as those obtained with TMSBr. The ease in which 5 and 6 are deprotected with TMSCl in chlorobenzene is in striking contrast to deprotection by heating with TMSCl alone, which is reported in the literature not to be effective in deprotecting adenosine diethylphosphonates[11].

Reaction (2) is illustrated below:

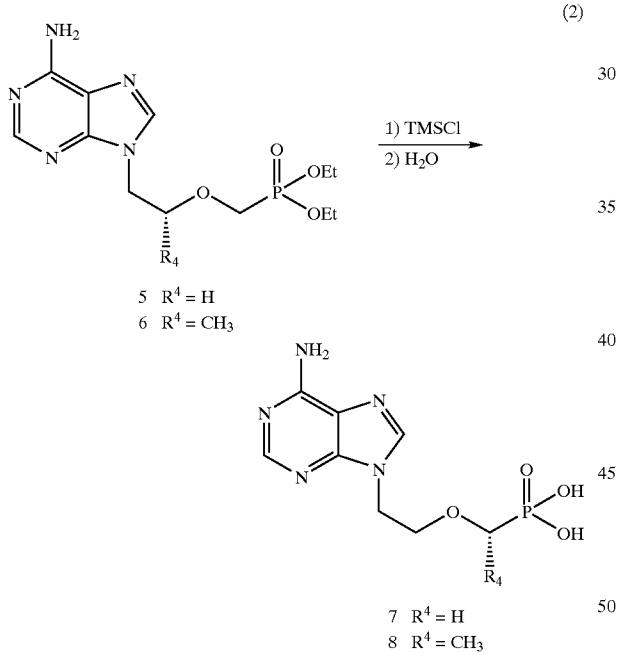

Specifically, diethyl PMEA 5 (41.1 g, 0.125 mol) and chlorobenzene (0.125 L) were charged to a 1L ACE™ glass pressure reactor (available from Ace Glass, Inc.) containing a thermowell and a pressure gauge. The contents were stirred while TMSCl (56 mL, 0.44 mol) was added carefully. The reaction vessel was purged with $N_2$, sealed, and heated to 125° C. The internal reactor pressure increased incrementally to a maximum of 30 psi after 9 h. The contents were cooled to RT at which time the pressure returned to ambient pressure and water (160 mL) was added with vigorous stirring. The layers were separated and the lower aqueous layer containing the product was collected. The aqueous layer was adjusted to pH=3.2 with 25% NaOH (~36 g), the resulting slurry cooled to 0° C. and the solid collected by vacuum filtration. Water (40 mL) was added to the wet cake, the resulting slurry was heated to 70° C. for 1 h, and then cooled to 0° C. The solid product was collected by vacuum filtration and dried under vacuum (50° C./28 mm Hg) affording 33.0 g (0.120 mol, 96%) PMEA 7 with NMR values consistent with those reported in the literature.[12]

In the same manner 48.3 g (0.140 mol) diethyl PMPA 6 was deprotected with 4.5 eq. TMSCl and yielded 30.3 g (0.105 mol, 75%) of PMPA 8. NMR data: $^1$H-NMR (300 MHZ, $D_2O$): δ=8.31 (s, 2H, adenine-2H, -8H), 4.39 (dd, J=14.3 Hz, 1H, $CH_2N$), 4.20 (dd, J=14.7 Hz, 1H, $CH_2N$), 3.89 (m, 1H, CH), 3.58 (dd, J=13.9 Hz, 1H, $OCH_2P$), 3.38 (dd, J=13.9 Hz, 1H, $OCH_2P$), 1.07 (d, J=6 Hz, 3H, $CH_3$). $^{31}$P-NMR (121 MHZ, $D_2O$), δ=15.79

Equivalent results were obtained when the process was scaled to 5 kg in a 30 gal. glass-lined Pfaudler reactor.

From the foregoing description, various modifications and changes in the composition and method will occur to those skilled in the art. All such modifications coming within the scope of the appended claims are intended to be included therein.

What is claimed is:

1. A method for dealkylation of phosphonate esters which method comprises:
   (a) combining a phosphonate ester and trimethylchlorosilane in a solvent in the absence of alkali iodide salts; and
   (b) maintaining the resulting reaction mixture under conditions wherein the phosphonate ester is converted to trimethylsilyl phosphonate.

2. The method according to claim 1 wherein said reaction mixture is maintained in a sealed vessel.

3. The method according to claim 1 which further comprises hydrolyzing said trimethylsilyl phosphonate to provide for a phosphonic acid or a salt thereof.

4. A method for dealkylation of phosphonate esters which method comprises:
   (a) adding a phosphonate ester to a solvent within a sealable container;
   (b) adding trimethylchlorosilane to the sealable container defined in (a) above;
   (c) sealing the container;
   (d) maintaining the sealed container under conditions wherein the phosphonate ester is converted to silyl phosphonate; and
   (e) hydrolyzing the silyl phosphonate to provide for the dealkylated phosphonic acid or a salt thereof.

5. The method according to either claim 1 or claim 4 wherein the phosphonate ester is represented by a compound of either formula I or II:

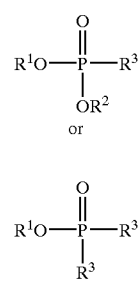

wherein $R^1$ and $R^2$ are independently selected from the group consisting of hydrogen, alkyl, substituted alkyl, alkenyl, substituted alkenyl, alkynyl, substituted alkynyl, cycloalkyl, substituted cycloalkyl, aryl, heteroaryl and heterocyclic; and $R^3$ is selected from the group consisting of alkyl, substituted alkyl, alkenyl, substituted alkenyl, alkynyl, substituted alkynyl, alkylene-O-alkyl, substituted alkylene-O-alkyl, alkylene-O-substituted alkyl, substituted alkylene-O-substituted alkyl, alkylene-S-alkyl, substituted alkylene-S-alkyl, alkylene-S-substituted alkyl, substituted alkylene-S-substituted alkyl, alkylene-O-alkyenyl, alkyene-O-substituted alkyenyl, aryl, heteroaryl and heterocyclic and salts thereof and with the proviso that, in formula I, at least one of $R^1$ and $R^2$ is other than hydrogen and in formula II, $R^1$ is not hydrogen.

6. The method according to claim 5 wherein the phosphonate ester is represented by the formula:

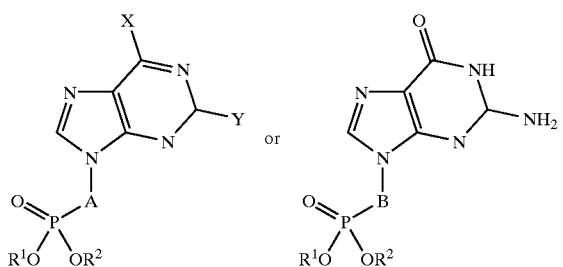

wherein A and B are selected from the group consisting of alkylene, substituted alkylene, alkylene-O-alkylene, alkylene-O-substituted alkylene, substituted alkylene-O-alkylene, substituted alkylene-O-substituted alkylene, alkylene-S-alkylene, substituted alkylene-S-alkylene, alkylene-S-substituted alkylene, substituted alkylene-S-substituted alkylene, alkylene-O-alkenylene, alkylene-O-substituted alkenylene, substituted alkylene-O-alkenylene, substituted alkylene-O-substituted alkenylene, alkylene-S-alkenylene, substituted alkylene-S-alkenylene, alkylene-S-substituted alkenylene, and substituted alkylene-S-substituted alkenylene; X is selected from the group consisting of hydrogen, hydoxyl and amino; and Y is selected from the group consisting of hydrogen and amino.

7. The method according to claim 5 wherein the phosphonate ester is represented by the formula:

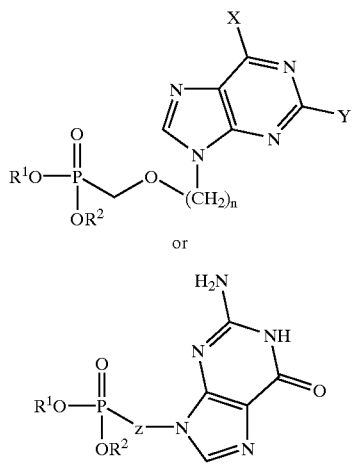

wherein X is selected from the group consisting of hydrogen, hydoxyl and amino; Y is selected from the group consisting of hydrogen and amino; Z is selected from the group consisting of alkylene, substituted alkylene and alkylene-O-alkylene; and n is an integer of from 1 to 10.

8. The method according to claim 1 wherein the solvent is selected from the group consisting of chlorobenzene, dimethylformamide, acetonitrile and dichloroethane, n-butylchloride, 2-butylchloride, n-pentylchloride, 2-chloropentane, 1-chlorooctane, trichloroethane, chloroform, cyclopentyl-chloride, chlorocyclohexane, chlorobenzene, 2-chlorotoluene, o-dichloro-benzene, 1-chloronaphthlene, 4-chlorobenzotrichloride, 2-chlorobenzotri-fluoride, 3-chlorobenzotrifluoride, 4-chlorobenzotrifluoride, chlorodibromo-methane, chlorodibromo-fluoromethane, benzene, toluene, o-xylene, propionitrile, valeronitrile, benzonitrile, dimethylacetamide, dimethylpropionamide, 1methylpyrrolidin-2-one, methyl acetate, ethyl acetate, isopropyl acetate, methyl propionate, ethyl propionate, methyl butyrate, ethyl butryate, methyl caproate, ethyl caproate, butyl acetate, ethyl isovalerate, methyl ethyl ketone, ethyl propyl ketone, methyl iso-butyl ketone, 3-methyl-2-butanone, and methyl iso-amyl ketone.

9. The method according to claim 8 wherein the compatible solvent is selected from the group consisting of chlorobenzene, dimethylformamide, acetonitrile and dichloroethane.

10. The method according to claim 1 wherein the solvent has a boiling point of about 60° C. or higher.

11. The method according to claim 1 wherein the solvent has a dielectric constant of at least about 5.

12. A method for dealkylation of bisphosphonate esters which method comprises:
(a) adding a bisphosphonate ester to a solvent within a sealable container wherein the bisphosphonate ester is represented by the formulas:

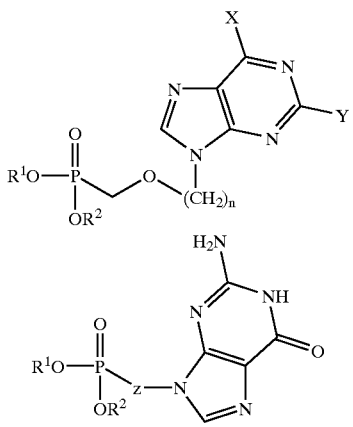

wherein $R^1$ and $R^2$ are independently selected from the group consisting of alkyl, substituted alkyl, alkenyl, substituted alkenyl, alkynyl, substituted alkynyl, cycloalkyl, substituted cycloalkyl, aryl, heteroaryl and heterocyclic; X is selected from the group consisting of hydrogen, hydoxyl and amino; Y is selected from the group consisting of hydrogen and amino; Z is selected from the group consisting of alkylene, substituted alkylene and alkylene-O-alkylene; and n is an integer of from 2 to 10;
(b) adding at least two stoichiometric amount of trimethylchlorosilane to the sealable container defined in (a) above;
(c) sealing the container;

(d) maintaining the sealed container under conditions wherein the bisphosphonate ester is converted to bis(silyl)phosphonate of the formula:

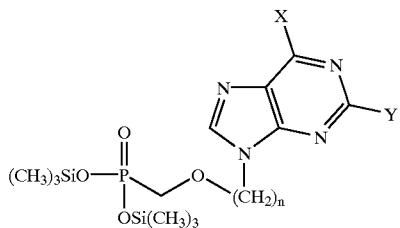

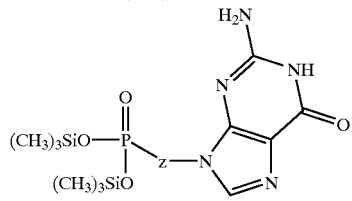

wherein X, Y, Z and n are as defined above; and (e) hydrolyzing the bis(silyl)phosphonate to provide for the dealkylated phosphonate of the formula:

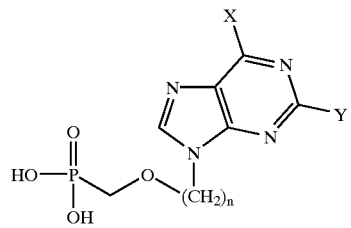

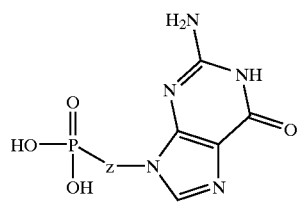

wherein X, Y, Z and n are as defined above; and salts thereof.

13. The method according to claim 12 wherein the bisphosphonate ester is of the formula:

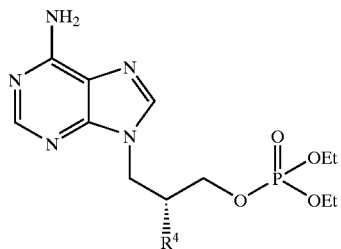

wherein $R^4$ is selected from the group consisting of hydrogen and methyl.

* * * * *